(12) United States Patent
Rubner et al.

(10) Patent No.: US 8,335,553 B2
(45) Date of Patent: Dec. 18, 2012

(54) CT-FREE SPINAL SURGICAL IMAGING SYSTEM

(75) Inventors: Joseph Rubner, Shoham (IL); Eli Zehavi, Haifa (IL); Leonid Kleyman, Acco (IL)

(73) Assignee: Mazor Robotics Ltd., Caesarea (IL)

( * ) Notice: Subject to any disclaimer, the term of this patent is extended or adjusted under 35 U.S.C. 154(b) by 609 days.

(21) Appl. No.: 12/442,737

(22) PCT Filed: Sep. 25, 2007

(86) PCT No.: PCT/IL2007/001194
§ 371 (c)(1),
(2), (4) Date: Mar. 25, 2009

(87) PCT Pub. No.: WO2008/038284
PCT Pub. Date: Apr. 3, 2008

(65) Prior Publication Data
US 2010/0106010 A1    Apr. 29, 2010

Related U.S. Application Data

(60) Provisional application No. 60/846,750, filed on Sep. 25, 2006.

(51) Int. Cl.
*A61B 5/05* (2006.01)
(52) U.S. Cl. ......... 600/407; 600/424; 600/425; 600/426
(58) Field of Classification Search .................. 600/407, 600/424–426
See application file for complete search history.

(56) References Cited

U.S. PATENT DOCUMENTS

| | | | |
|---|---|---|---|
| 6,198,794 B1 * | 3/2001 | Peshkin et al. | 378/42 |
| 6,423,077 B2 * | 7/2002 | Carol et al. | 606/130 |
| 6,837,892 B2 | 1/2005 | Shoham | |
| 2002/0082492 A1 * | 6/2002 | Grzeszczuk | 600/407 |
| 2003/0073901 A1 * | 4/2003 | Simon et al. | 600/424 |

(Continued)

FOREIGN PATENT DOCUMENTS
WO  WO 2006/075331  7/2006
WO  WO 2008/038283  4/2008

OTHER PUBLICATIONS

PCT Int'l Search Report mailed Aug. 20, 2008 and Written Opinion of the ISA, mailed Aug. 20, 2008 in PCT/IL2007/01194.

*Primary Examiner* — Long V. Le
*Assistant Examiner* — Ellsworth Weatherby
(74) *Attorney, Agent, or Firm* — Daniel J. Swirsky; AlphaPatent Associates Ltd.

(57) ABSTRACT

A system and method for generating three dimensional CT-type information from a conventional C-arm fluoroscope imaging system. A small number of fluoroscope images are used, taken from angles whose pose is determined by means of a three-dimensional target attached to the region of interest, aided by the participation of the surgeon or an image processing routine to pinpoint known anatomical features in the region of interest of the patient. This procedure enables the reconstruction of virtual images in any desired plane, even in planes other than those accessible by the C-arm imaging process, such as the axial plane of a vertebra. Use of this system and method of marking of the feature to be treated in a small number of angularly dissimilar images, enables the generation of CT-type information which can be used to accurately align a robotically guided surgical tool with the anatomical feature.

7 Claims, 7 Drawing Sheets

U.S. PATENT DOCUMENTS

| | | |
|---|---|---|
| 2004/0171924 A1 | 9/2004 | Mire et al. |
| 2005/0245817 A1* | 11/2005 | Clayton et al. ................. 600/424 |
| 2006/0050943 A1* | 3/2006 | Ozaki et al. ................... 382/131 |
| 2006/0098851 A1 | 5/2006 | Shoham et al. |
| 2007/0100258 A1 | 5/2007 | Shoham et al. |
| 2008/0071272 A1 | 3/2008 | Shoham et al. |

* cited by examiner

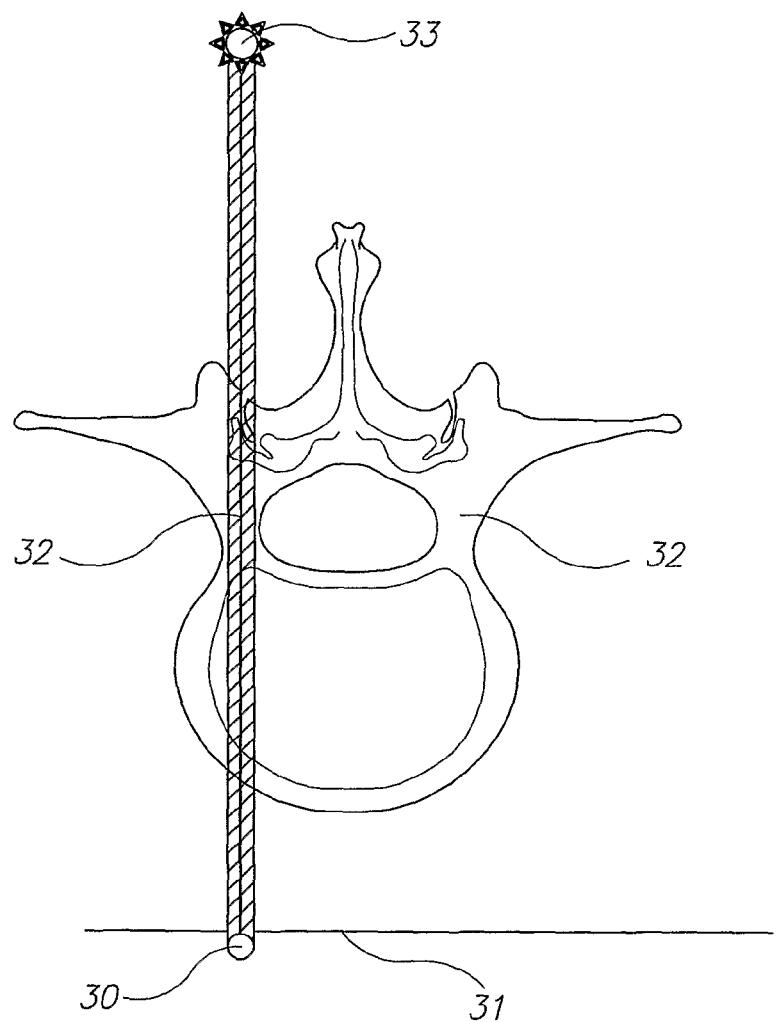
FIG.3
  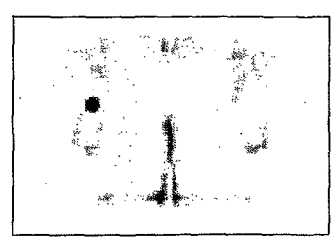
FIG.4A     FIG.4B     FIG.4C

CT-FREE SPINAL SURGICAL IMAGING SYSTEM

CROSS-REFERENCE TO RELATED APPLICATIONS

This application is a U.S. National Phase Application under 35 U.S.C. 371 of PCT International Application No. PCT/IL2007/001194, which has an international filing date of Sep. 25, 2007, and which claims priority from U.S. Provisional Patent Application No. 60/846,750, filed Sep. 25, 2006, both of which disclosures are hereby incorporated by reference.

FIELD OF THE INVENTION

The present invention relates to the field of CT imaging, especially as applied to the spinal surgery using a conventional C-arm fluoroscopic image system

BACKGROUND OF THE INVENTION

There exist robotic platforms for enhancing spine surgical procedures such as the SpineAssist™ system, as supplied by Mazor Surgical Technologies Ltd, of Caesarea, Israel. This system enables accurate spinal surgery to be readily performed with minimal intervention. Such systems can be used for guidance in pedicle screw insertion for spine fusion procedures. SpineAssist™ itself focuses on two key steps: Preoperative planning of the surgical procedure to be performed and Intra-operative spatial positioning and orientation of surgical tools, such as a drill guide for drilling pedicle screw holes. Additional applications which can be performed using such systems include vertebroplasty, tumor evacuation, artificial disc placement, cervical and thoracic fusion procedures, and more. Additional applications of the robot used in the SpineAssist™ system have been described in U.S. Pat. No. 6,837,892, and in co-pending U.S. patent application Ser. Nos. 10/517,846, 10/557,048, 10/595,305, and in International Patent Application No. PCT/IL2006/000056 published as WO 2006/075331.

Computer aided surgery applications, such as the above described robotic systems, generally use a preoperative CT of the patient in order to perform the procedure planning. Acquiring a CT scan of a patient requires expensive resources that are not always present or available in hospitals. In addition, the need of a CT scan prior to the operation extends the overall time of the procedure, time which is not always available. Additionally, CT imagers, because of their size and weight, are almost invariably located in dedicated sites, and it is exceedingly rare to find a CT imager located in an operating room where the surgical procedure is being conducted. On the other hand, during the operation itself, it is possible to acquire X-ray fluoroscopic images using a mobile C-arm system, which is commonly present in the operation room. The SpineAssist™ platform, for instance, acquires and uses two such fluoroscopic images to align the CT on which the planning was done, with the patient position during the surgery. The alignment is done by means of a registration procedure using a known 3D target which is attached to the vertebra during the surgery, and whose position can be accurately determined in the fluoroscopic images.

Unfortunately, it would not be recommendable to perform the procedure planning using C-arm fluoroscopic images acquired in the operating room, due to the fact that only AP (anteroposterior), LT (lateral), or in-between angle images can be taken. AX (axial) images, which are important in the planning procedure, cannot be acquired using a mobile C-arm. The importance of the AX view for the preoperative planning is apparent from FIG. 1, which is a view of a control screen showing from an axial view, a pair of pedicle screws inserted into a vertebra. As is evident from here, only in an axial view is it possible to accurately view the intended position of the screws, to ensure that they do not cause damage to the spinal cord, or break out of the pedicle. Similar consideration apply to most surgical procedures, where the limitation of imaging in one plane only may be disadvantageous.

There therefore exists a need for generating AX views of the vertebrae or other surgical site, using a standard C-arm fluoroscope imaging system, without the need for an expensive CT system, and with the ability to conveniently generate such views during a surgical procedure. Such a system is called in this application a CT-free imaging system.

The disclosures of each of the publications mentioned in this section and in other sections of the specification are hereby incorporated by reference, each in its entirety.

SUMMARY OF THE INVENTION

The present invention seeks to provide a new system and method for generating three dimensional CT-type information from a conventional C-arm fluoroscope imaging system, which provides two-dimensional images. The surgeon is presented with this information in such a manner that a surgical procedure can be carried out accurately and safely, using a computer aided guidance system, but without the use of a preoperative CT scan. The system and method use a comparatively small number of fluoroscope images, taken from angles whose three dimensional pose (angular orientation and position) is determined by means of a three-dimensional target attached to the region of interest. Although a conventional CT image constructed from only a small number of fluoroscope scans would be of generally low quality and resolution, according to the present invention, the imaging information is augmented by the participation either of the surgeon or of an image processing routine in pinpointing known anatomical features in the region of interest of the patient. This procedure enables the reconstruction of virtual images in any desired plane, and in particular, in planes other than those accessible by the C-arm imaging process, such as the axial plane of a vertebra. Use of this system and method enables the generation of CT-type information of adequate quality without the need to use typically of the order of a hundred or more images for the reconstruction, as is typically performed in conventional CT-systems. The addition, according to the present invention, of the defining of specific anatomic features in the region of imaging interest increases the information content to such an extent that even with such a small number of fluoroscope images, CT data of acceptable quality is obtained.

The system according to the present invention, preferably comprises the following components, preferably used in the following manner:
(i) A target, incorporating a three dimensional array of X-ray opaque marker points, which are visible on the fluoroscope images, is attached to the patient such that the 3D pose of the C-arm can be precisely determined relative to the target position and hence relative to the region of interest in the patient.
(ii) A set of several fluoroscopic images, and preferably of 5 to 10 fluoroscopic images is acquired from different angles. The angles are determined according to the specific procedure being performed, but images are typically taken at angular intervals of the order of every 5 to 10 degrees. According to another preferred embodiment of the system, the C-arm is used to acquire a continuous video sequence while the C-arm is rotated, to capture multiple angles, from which are selected the few angles required for performing the preferred methods of the present invention.

(iii) The target is identified in each of the acquired fluoroscopic images, the 3D pose of the X-ray source is computed and for each of the images, the location and angular orientation of the image plane (i.e. the detector (camera) plane) relative to the source is determined. This means that the image planes for images taken at different angles can be related to each other, and the axial view thus constructed.

(iv) Relevant anatomic features in the images are identified and marked (automatically by image processing or manually by the surgeon). Any point selected on a fluoroscope image implies a 3D ray between the 3D location of the X-ray source in the space co-ordinates, and the 3D location of the real-life point which was marked in the fluoroscope image.

(v) Using triangulation of the rays deduced from the different flouroscope images, the 3D pose of the feature itself may be reconstructed in real-life co-ordinate space.

Although this concept is general and can be applied for many applications and in different parts of the body, this patent application uses pedicle screw insertion as an example of the application of the methods of the present invention. It is to be understood however, that the invention is not meant to be limited to such an application.

There is therefore provided in accordance with a preferred embodiment of the present invention, a method of determining a path through an anatomical feature of a subject, comprising the steps of:
(i) disposing a target having an array of X-ray opaque markers in a three dimensional pattern in the region of the anatomical feature of the subject,
(ii) providing an X-ray source to generate fluoroscopic images of the region of the anatomical feature of the subject,
(iii) taking at least two fluoroscopic images of the anatomical feature of the subject, the images being aligned in the region of the anterior-posterior orientation,
(iv) marking on each of the at least two fluoroscopic images the estimated position of the center of the feature,
(v) using the target to define the spatial position of the source,
(vi) generating an axial plane virtual image of the anatomical feature of the subject, including a line for each image alignment, the line on each image being computed to run between the source and the marked position, and
(vii) using the data relating to the lines to determine the path.

In the above described method, the anatomical feature may preferably be a pedicle of a vertebra of the subject, and the path is a safe path for the insertion of a pedicle screw. In such a case, the data relating to the lines is preferably used to provide instructions to a device for drilling pedicle screw holes along the safe path.

In any of the above described methods, the marking may preferably be performed either by means of operator intervention, or by means of an image processing procedure.

In accordance with yet another preferred embodiment of the present invention, there is provided a method for generating an axial image of an anatomical feature, comprising the steps of:
(i) providing an X-ray source to generate fluoroscopic images of the subject,
(ii) disposing a target having an array of X-ray opaque markers in a three dimensional pattern in the region of the anatomical feature of the subject,
(iii) taking at least two fluoroscopic images of the anatomical feature, aligned at lateral angles close to each other,
(iv) marking a predetermined feature on the images of the anatomical feature,
(v) using information from images of the target to generate an axial image of lines from the source to the feature, and
(vi) using the axial image to direct a surgical tool to the feature at an angle predetermined from the lines on the axial image. The marking may preferably be performed either by means of operator intervention, or by means of an image processing procedure. Additionally, the at least two fluoroscopic images may preferably be taken from a video sequence of the vertebra as the source is moved relative to the subject. In any of the above described methods, the anatomical feature may preferably be a pedicle of a vertebra of the subject.

There is further provided in accordance with yet another preferred embodiment of the present invention, a system for generating an axial image of a vertebra from a small number of fluoroscope images, the system comprising:
(i) a target for attaching to the spine of the subject in the region of the vertebra, and
(ii) a computing system for processing and displaying the fluoroscope images, the computing system comprising:
(iii) a marking system such that a predetermined feature may be marked on the images of the vertebra, and
(iv) a line generator using information from images of the target to generate an axial image of lines from the source to the marked feature,
(v) wherein the axial image is used to direct a surgical tool to the feature at an angle predetermined from the lines on the axial image.

In the above described system, the lines are preferably utilized to estimate the three dimensional pose of the feature. Additionally, the marking system may preferably comprise an operator actuated marking device, or an image processing module adapted to recognize the predetermined feature. Additionally, in any of the above described embodiments of this system, the predetermined feature may preferably be the central region of a pedicle of the vertebra of the subject.

In accordance with still another preferred embodiment of the present invention, there is provided a method of determining a path through an orthopaedic feature of a subject, comprising the steps of:
(i) attaching a target to the subject in the region of the orthopaedic feature,
(ii) providing an X-ray source to generate fluoroscopic images of the subject,
(iii) taking at least two fluoroscopic images of the orthopaedic feature, aligned in the region of the anterior-posterior orientation,
(iv) marking on each of the fluoroscopic images the estimated position of the center of the feature,
(v) using the target to define the spatial position of the source,
(vi) generating an axial plane virtual image of the orthopaedic feature, comprising lines for each image alignment, computed to run between the source and the marked positions, and
(vii) using the data relating to the lines to determine the path.

In this method, the orthopaedic feature may preferably be a pedicle of a vertebra of the subject, and the path a safe path for the insertion of a pedicle screw.

BRIEF DESCRIPTION OF THE DRAWINGS

The present invention will be understood and appreciated more fully from the following detailed description, taken in conjunction with the drawings in which:

FIG. 3 shows a virtual axial view of the vertebra of FIG. 2, showing a stripe running from the X-ray source through the marked center of the pedicle;

FIGS. 4A to 4C show further fluoroscope images similar to that of FIG. 2, but taken from three different obliquely lateral angles;

DETAILED DESCRIPTION OF PREFERRED EMBODIMENTS

Figure 1:
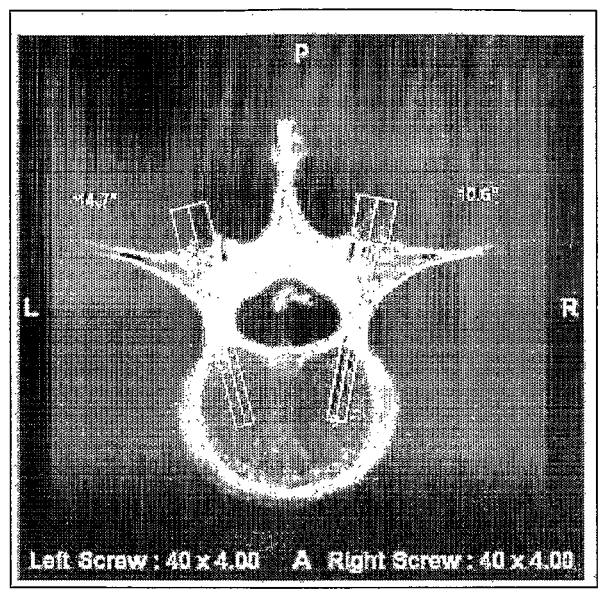
FIG. 1 shows schematically a CT-type of axial view of a vertebra showing a pair of pedicle screws inserted therein.
Figure 2:
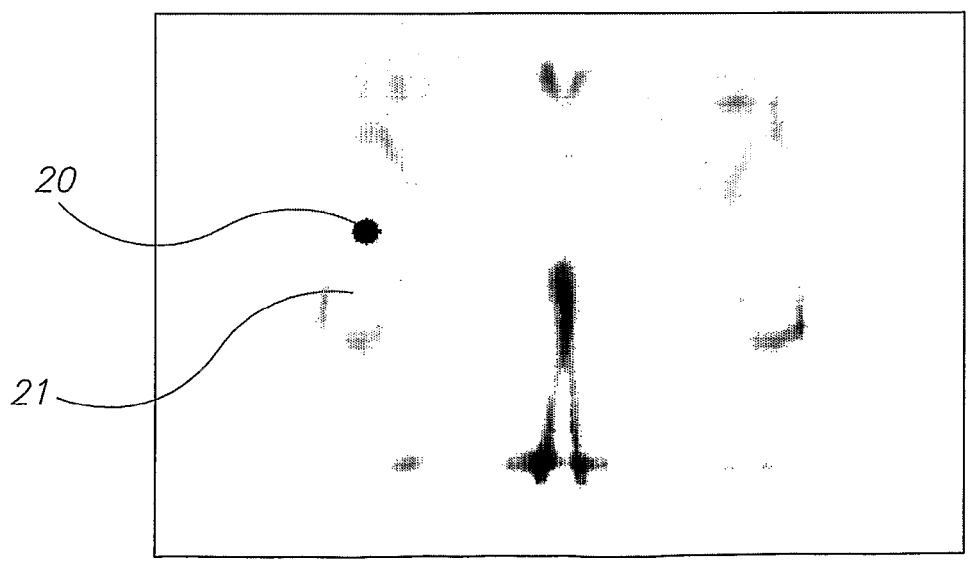
FIG. 2 is an acquired AP fluoroscopic image of a vertebra, showing a pedicle with its central position marked.

Reference is now made to FIG. 2, which shows an acquired AP fluoroscopic image of a subject's vertebra. The surgical procedure to be performed on this vertebra, according to this preferred application of the present invention, is the drilling of a screw hole into the pedicle at such an angle that the hole will neither break out of the pedicle, nor enter the spinal channel where serious damage could be caused. On this image, a spot 20 is marked at what appears to the surgeon to represent the best estimated position of the center of the left pedicle 21. The pedicle appears as an elliptical shape due to the concentration of bone density on the cylinder-like pedicle surface. According to a further preferred embodiment of the invention, the pedicles may be identified automatically using image processing methods.

Once the 3D pose of a fluoroscope image is determined using the target image data, a point drawn on the image represents in the real-life world, a ray between the 3D position of that point in space and the X-ray source, whose position in space is now also known relative to the target. In the image shown in FIG. 2, this spot thus represents a line running from the X-ray source to the center of the pedicle.

Reference is now made to FIG. 3, where this virtual line is shown as a stripe displayed on a virtual axial image of the vertebra being imaged, the line running from the X-ray source 33 to the center of the pedicle 32, and perpendicular to the image plane 31. The marked spot 30 is seen on the image plane when looking into the image. The position of this line is computed relative to the target plate, as the pose of the C-arm source relative to the target can be determined from the position of the opaque spheres of the target on the images.

Reference is now made to FIGS. 4A to 4C which show further fluoroscope images taken from three different obliquely lateral angles, with the best estimated position of the centers of the pedicle marked on each of them.

Figure 5:
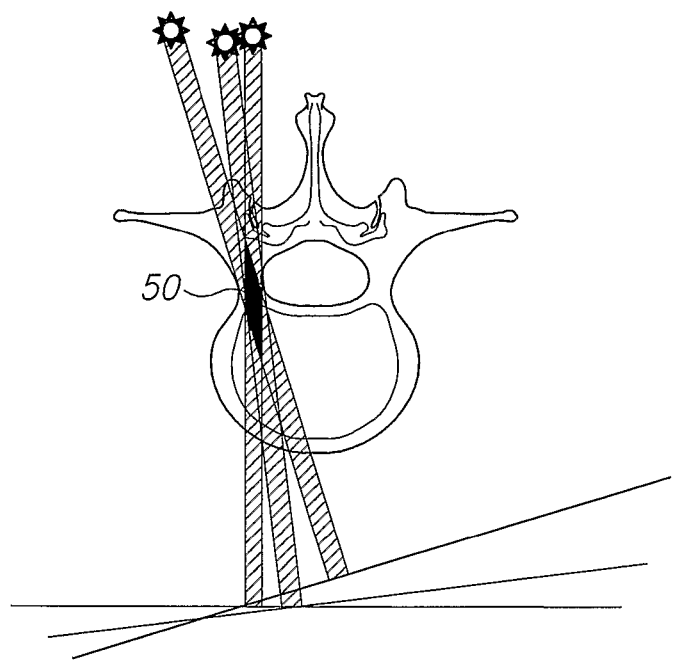
FIG. 5 shows a virtual axial image of the vertebra, with the projection of the beams of FIGS. 4A to 4C shown in the virtual axial plane.

Reference is now made to FIG. 5, which shows a virtual axial image of the vertebra, with the projection of the beams of FIGS. 4A to 4C shown in the virtual axial plane. The intersection of the stripes reveals a "safe" region 50 in the pedicle area, where an inserted screw would not penetrate the spinal cord passage on one side, and would not break out of the vertebrae on the other side and damage the nerve roots.

In practice, however, the axial image shown in FIG. 5 is not accessible, but using the preferred methods of the present invention, the screws that need to be inserted through the pedicles can still be precisely positioned, even without clearly seeing the axial image itself. The robotic control of the screw insertion system can be programmed to use the data of the virtual axial image of FIG. 5, typically to align a drill guide tube in such an orientation that the drilled screw hole will pass through the center of the shaded "safe" region. The robotic coordinate system is registered to the co-ordinate system of the virtual axial image by mounting the robot base in a known position relative to the target. According to one preferred embodiment, this is achieved by mounting the robot base onto the same base as is used to mount the target. Thus, a combination of the marks made by the surgeon on a small number of fluoroscopic images, together with the knowledge generated from the use of the target plate regarding the 3-dimensional position of the source for every marked anatomical landmark on the fluoroscope image, enables the robotic positioning system to direct the screw drilling almost as if the virtual axial image had been a real CT generated axial image.

In this respect, the system and method of the present invention simulates the methodology of a regular CT scanning procedure, with the important difference that:

(i) it is performed on a small predefined region of interest;
(ii) it uses a small number of images, and
(iii) it uses the surgeon's judgment and intervention, or image processing software, to assist in defining the data input for generating the output of the "pseudo-CT scan", namely a drilling direction and location which is safely centralized on the intended target.

Figure 6:
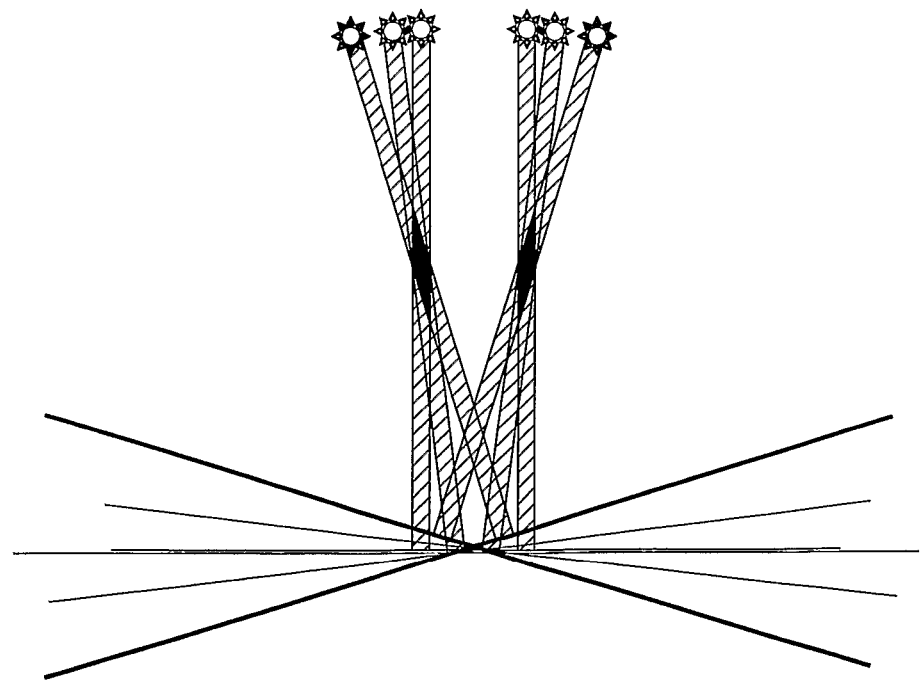
FIG. 6 shows the procedure illustrated in FIG. 5 but performed for both the left and the right pedicles.

The procedure can be performed for both the left and the right pedicles, as shown in FIG. 6.

Figure 7:
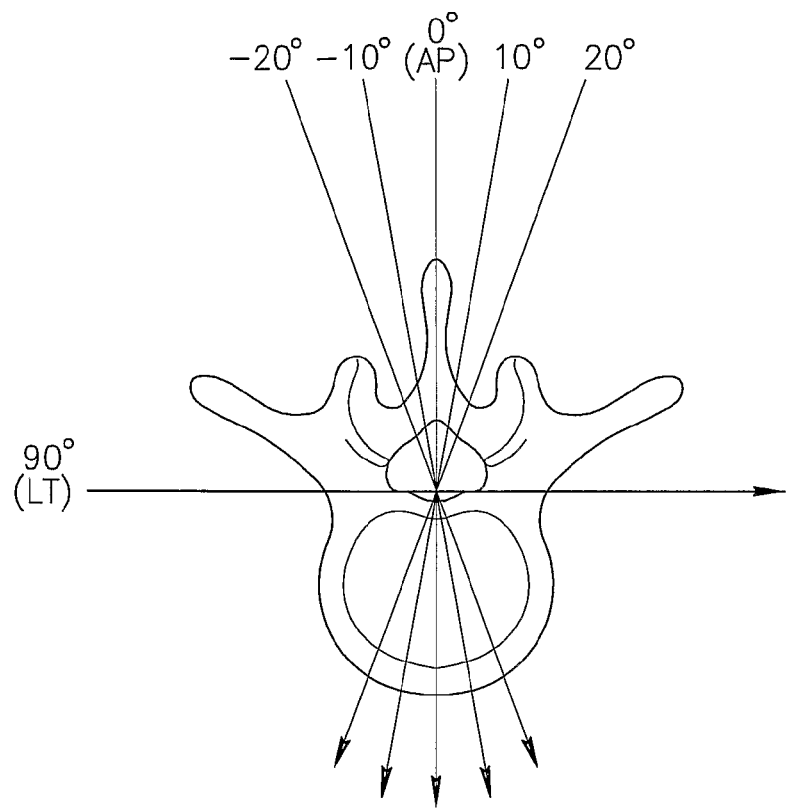
FIG. 7 shows schematically an example of a vertebra with four orientations close to the AP direction for use in generating the virtual axial plot shown in FIG. 6.

The detailed method can be described as follows, again using pedicle screw insertion as a preferred example. During the operation, using the C-arm fluoroscope system, a single LT fluoroscopic image and at least two, or more advantageously, at least three images at angles preferably close to the AP orientation are taken for each of the pedicles. Often, the exact AP image can be used for both pedicles, resulting in a total of six preferred images: five of them close to or at the AP orientation, and an LT image, as shown in FIG. 7. According to another preferred embodiment of the invention, the fluoroscopic images can be acquired from a video sequence by using a continuous motion mode of the C-arm, and using selected frames for marking by the surgeon.

In effect, only two images are essentially required for performing the triangulation, but the use of at least three images provides a more robust measurement. Thus for instance, careful inspection of the pedicle images may enable the surgeon to generate acceptable results using only two images, since it may be possible to estimate when the imaging direction is close to being directly along the length of the pedicle, such as by analyzing the cross sectional size, the shape and the image shading of the pedicle image. If such a direction can be accurately estimated, then the need for a larger number of images at different angles to define the pedicle direction is reduced, and two images may well suffice. However, such an embodiment puts more responsibility on the surgeon's judgment, as compared with the three or more directional procedure, which is less prone to error.

The five images typically acquired in the vicinity of the AP direction are used to identify the pedicle positions on the axial plane and to orient the AP direction of the axial plane. The AP image itself is used for both of the pedicles, and two more images are used for each of the pedicles, preferably at the preferred angles shown in FIG. 7. The single LT image is used to orient the LT direction of the axial plane and to identify the pedicle area in the axial plane.

Fluoroscope images in the vicinity of the AP orientation show pedicles as ellipses. The surgeon clicks on what he estimates to be the pedicle centers in the relevant images, thereby entering into the system the perceived lines between the X-ray source and the pedicle centers for the alignment of each image. Relevant images are those where the pedicle cross section is close to being parallel to the image plane, for instance at angles of −20°, −10°, 0° for the left pedicle and 0°, −10°, −20° for the right pedicle. In the case that the continuous mode of the C-arm motion is used, the pedicles are perceived by the motion created by playing the video sequence. Although the video display enhances the view of the pedicles, In order to mark the center of the pedicle for selected angles, it is necessary to select individual images from the video sequence. In the co-pending PCT application entitled "C-arm Computerized Tomography System", methods are described whereby three dimensional reconstruction can be obtained from a video sequence of fluoroscope images, without the need to point at the specific feature being imaged.

Figure 8:
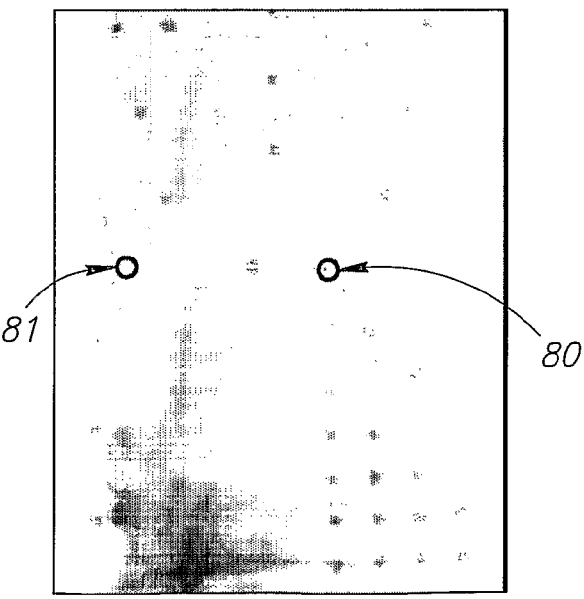
FIG. 8 is a schematic representation of a fluoroscope AP image taken of the spine of a subject, showing the pedicles to be operated on marked by the surgeon.

Reference is now made to FIG. 8, which is an actual fluoroscope AP image taken of the spine of a subject. The pedicles are clearly visible at the outer extremities of the vertebrae, and the pedicles of the vertebra to be operated on have been marked 80, 81 by the surgeon, preferably using the computing system cursor, whether a mouse, or a touch screen or an alternative marking device.

Marking a point on such a 2D image is equivalent to generating a line in real 3D space from the marked point to the X-ray source, whose coordinate relative to the target can be calculated using the distribution of the target's opaque spheres on the X-ray image.

The same method is repeated for all of the images taken at the different angles. Since each line passes from the X-ray source, through the pedicle center to the image plane, the result of this is the generation of a bundle of lines or strips in space, whose common intersection is the location of the pedicle "safe zone" relative to the target coordinates.

Figure 9:
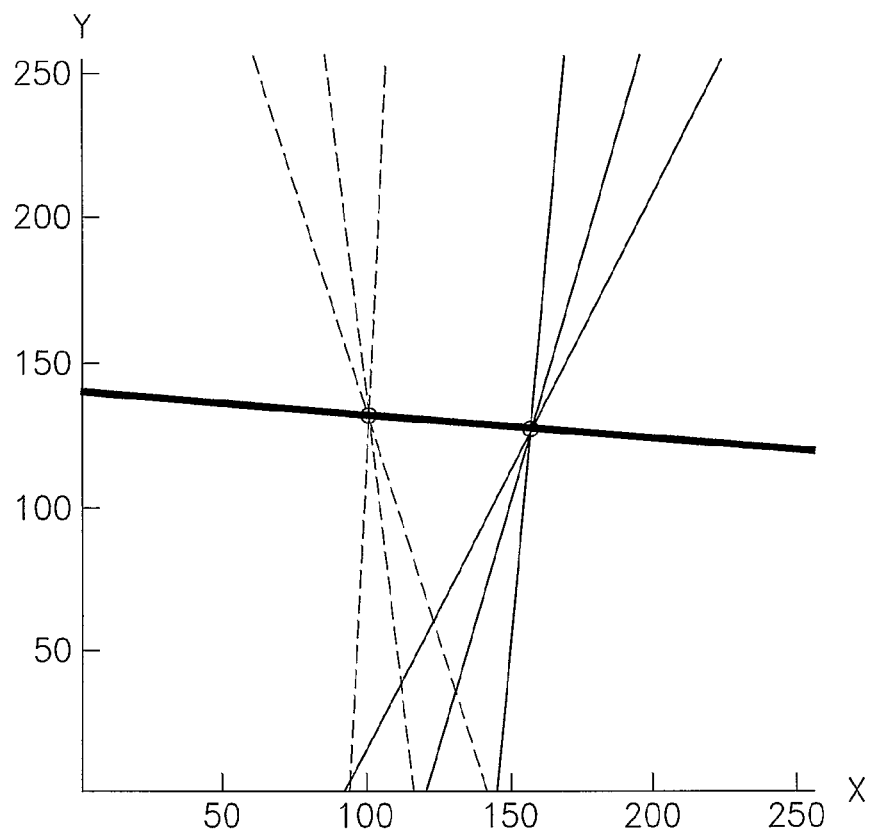
FIG. 9 is an updated axial plane image on which lines defined by the user selections have been projected.

At this point in the procedure, an updated axial plane image has been generated, on which the lines defined by the user selections have been projected. This is shown in FIG. 9. The dotted and full groups of lines represent the spatial lines from the source and through the two respective pedicles. The pedicle centers are marked as circles at the intersections of each group of spatial lines.

A robot located in a known position relative to the target can therefore point to the pedicle "safe zone" direction along which the surgeon drills to insert the pedicle screw. The robot co-ordinates is registered to the three dimensional co-ordinate system of the source/pedicle/image-plane lines since the robot has been mounted in a known position and orientation relative to that co-ordinate system, as described hereinabove.

Figure 10:
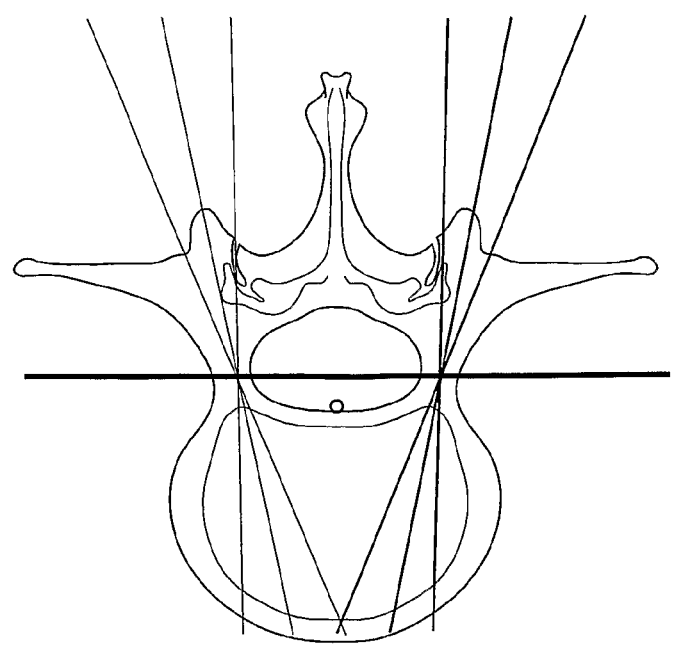
FIG. 10 shows a schematic representation of a preoperative CT image of the vertebra shown in FIG. 8, onto which are imposed the lines of FIG. 9.

Reference is now made to FIG. 10, which shows an actual preoperative CT image of the vertebra shown in FIG. 8, onto which are imposed the lines of FIG. 9, generated by the system from the pedicle markings on the intraoperative fluoroscope images. As is observed, the results validate the accuracy of the system and methods of the present invention.

Figure 11:
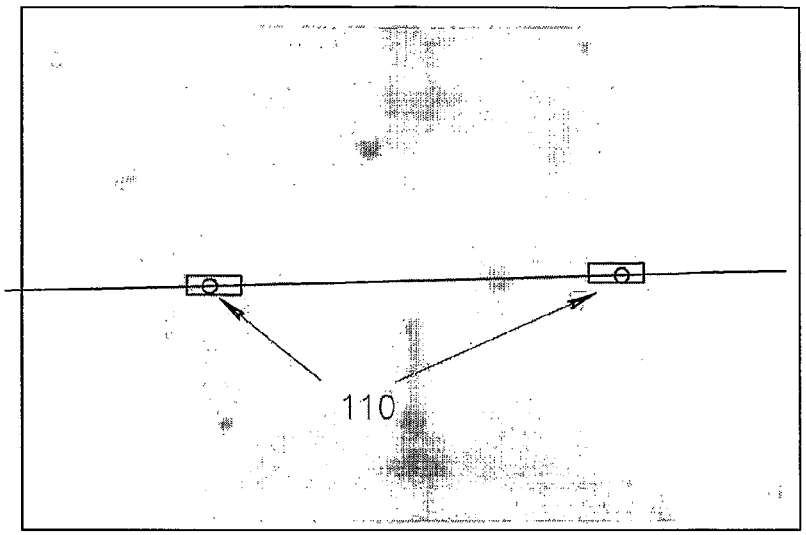
FIG. 11 depicts a safe zone marked in the fluoroscope image of a vertebra to be treated.

By selecting a single point on the fluoro images, thin line paths result on the virtual axial image. In order to obtain an estimate of the actual width of the pedicle in order to be able to plan the screw insertion, the user is allowed to select, together with the center of the pedicle, also a safe zone 110 for each of the selected pedicle. A safe zone is the area to the left and right of the center of the pedicle that the user believes is inside the pedicle. This is shown in the fluoroscope image of a vertebra depicted in FIG. 11.

Using the safe zones, sufficient information is available to determine the position and orientation of the screws, using the intersection of the safe zones. This is shown in FIG. 12, where the thin line paths have been replaced by broader swathes to represent the width of the safe zones.

Figure 12:
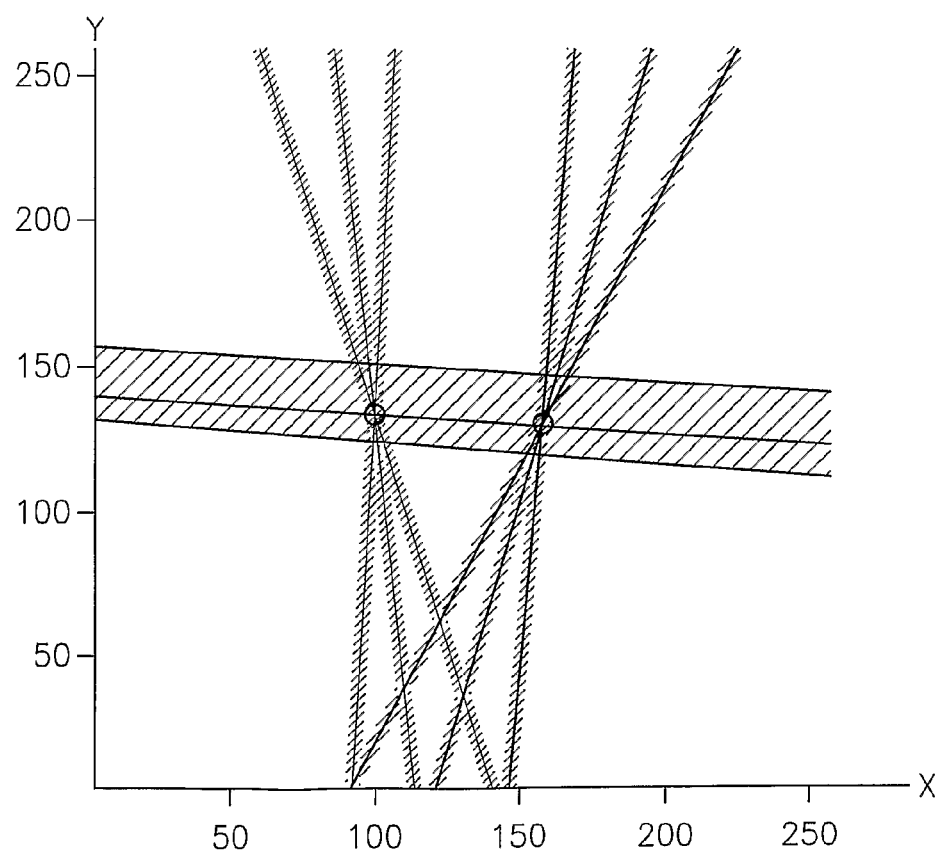
FIG. 12 shows the paths of FIG. 9, but broadened to include the surgeon-defined safe zones, such that the thin line paths have become broader swathes to represent the width of the safe zones.
Figure 13:
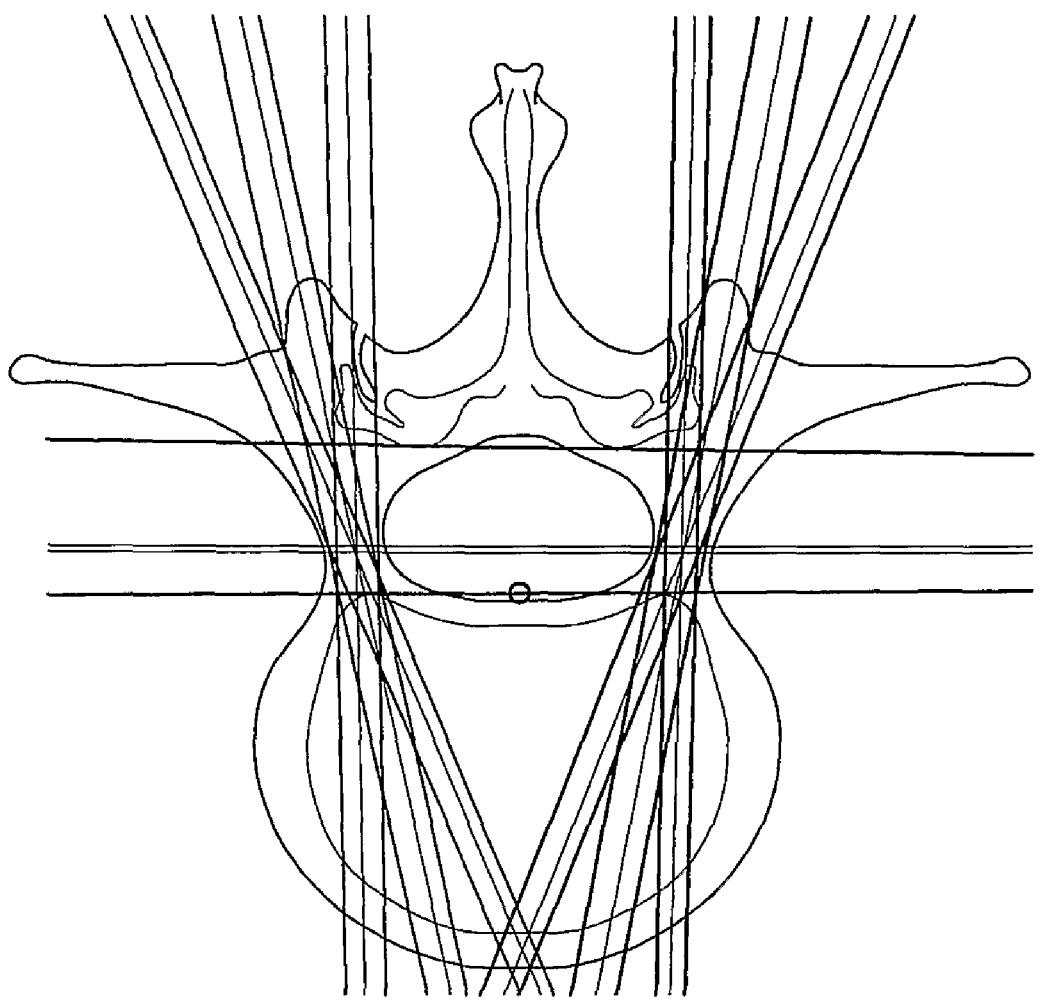
FIG. 13 is a plot similar to that of FIG. 10, but using the safe zone widths, showing the outcome of superimposing the results obtained from the virtual axial view of FIG. 12 onto a preoperative CT image.

FIG. 13 is a plot similar to that of FIG. 10, but using the safe zone widths, showing the outcome of superimposing the results obtained from the virtual axial view of FIG. 12, onto a preoperative CT image. The outcome verifies the correctness of the method. The outer two horizontal lines represent the safe zone selected in the LT image.

According to further preferred embodiments of the present invention, it is possible to extend the method described above with the following two methods.

As the complete 3D geometry of the images (X-ray and image positions) is known, it is possible to try and solve the inverse problem—the reconstruction of the axial plane from the projections, for example, by using an inverse-Radon transformation, or any other reconstruction method. For this purpose, 5 fluoro images may not suffice, and the acquisition process will preferably use a continuous imaging mode of the C-arm, preferably using a video sequence of images. This way, the C-arm is rotated and in a short time, sufficient fluoroscope images are acquired for the reconstruction. As in the previous method, the pose of each image will be determined using the target. According to this preferred method, because of the larger number of images available, a three dimensional volumetric model can be generated even without marking the pedicle, or other anatomic feature of interest.

According to a further preferred method, the 6 acquired images, or the video sequence acquired in the continuous mode of the C-arm, can be used together with a standard 3D template model of the vertebra, and a search performed for a 3D non-rigid transformation that will minimize the discrepancies between the images and the appropriate projection of the transformed model.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. A method of determining a path for performing a surgical procedure through an anatomical feature of a subject, comprising the steps of:

disposing a target having an array of X-ray opaque markers in a three dimensional pattern, in the region of said anatomical feature of said subject, and in a location fixed relative to said anatomical feature of said subject;

providing an X-ray source to generate fluoroscopic images of said region of said anatomical feature of said subject, including said target;

taking at least two fluoroscopic images of said anatomical feature of said subject including said target, said images being aligned in a generally anterior-posterior orientation;

marking on each of said at least two fluoroscopic images the estimated position of the center of said anatomical feature;

using said target to define the spatial position of said source relative to said anatomical feature of a subject;

generating an axial plane virtual image of said anatomical feature of said subject, including a line for each image alignment, said lines for each image alignment being computed to run between said source and said marked position; and using the intersection of said lines to generate a safe zone for performing said surgical procedure through said anatomical feature.

2. A method according to claim 1 and wherein said anatomical feature is a pedicle of a vertebra of the subject.

3. A method according to claim 2 and wherein said safe zone is used to provide instructions to a device for drilling pedicle screw holes.

4. A method according to claim 1 and wherein said marking is performed by means of operator intervention.

5. A method according to claim 4 and wherein said marking is performed by means of an image processing procedure.

6. A method of determining a path through an orthopedic feature of a subject, comprising the steps of:

attaching a target to said subject in the region of said orthopedic feature;

providing an X-ray source to generate fluoroscopic images of said orthopedic feature of said subject;

taking at least two fluoroscopic images of said orthopedic feature, said images aligned in a generally anterior-posterior orientation;

marking on each of said fluoroscopic images the estimated position of the center of said orthopedic feature;

using said target to define the spatial position of said source relative to said orthopedic feature of said subject;

generating an axial plane virtual image of said orthopedic feature, comprising lines for each image alignment, said lines to run between said source and said marked positions; and using the data relating to said lines to determine said path through said orthopedic feature of said subject.

7. A method according to claim 6 and wherein said orthopedic feature is a pedicle of a vertebra of the subject, and said path is a safe path for the insertion of a pedicle screw.

* * * * *